United States Patent
Glascock et al.

(10) Patent No.: US 6,813,950 B2
(45) Date of Patent: Nov. 9, 2004

(54) PHASED ARRAY ULTRASONIC NDT SYSTEM FOR TUBES AND PIPES

(75) Inventors: David Glascock, Spring, TX (US); Noël Dubé, St-Rédempteur (CA); Vincent Pasquer, Forges les bains (FR); Laurent Butin, St-Benoit (CA)

(73) Assignee: R/D Tech Inc., Québec (CA)

( * ) Notice: Subject to any disclaimer, the term of this patent is extended or adjusted under 35 U.S.C. 154(b) by 0 days.

(21) Appl. No.: 10/206,012

(22) Filed: Jul. 25, 2002

(65) Prior Publication Data

US 2004/0016299 A1 Jan. 29, 2004

(Under 37 CFR 1.47)

(51) Int. Cl.[7] .............................................. G01N 29/00
(52) U.S. Cl. ........................................ 73/633; 73/622
(58) Field of Search ........................ 73/632, 633, 637, 73/638, 639, 618–622, 624–629

(56) References Cited

U.S. PATENT DOCUMENTS

| | | | | |
|---|---|---|---|---|
| 3,402,598 A | * | 9/1968 | Colgate ........................ 73/629 |
| 3,529,465 A | * | 9/1970 | Kleesattel et al. ............. 73/577 |
| 5,024,093 A | * | 6/1991 | Sasaki et al. .................. 73/633 |
| 5,473,943 A | * | 12/1995 | Schoenen et al. .............. 73/644 |
| 5,485,751 A | * | 1/1996 | Karbach et al. ............... 73/618 |
| 5,974,889 A | * | 11/1999 | Trantow ........................ 73/624 |

\* cited by examiner

*Primary Examiner*—Helen C. Kwok
(74) *Attorney, Agent, or Firm*—William H. Eilberg

(57) ABSTRACT

One or more phased array ultrasonic probes in the shape of conical section arcs, or an entire conical section ring, emit beams at a fixed incident angle with respect to the outer surface of a tube or pipe under inspection. At any given moment, these beams strike the tube at a single small entry zone from number of different directions. After being refracted at the inspection angle corresponding to the fixed angle of incidence, defects having longitudinal, transverse and oblique orientations are detected in the three-dimensional volume of the tube wall. The number of entry zones required for complete coverage of the outer surface of the tube is a function of the size of the tube, the speed at which it passes through the inspection station and the rate of rotation of the tube.

18 Claims, 13 Drawing Sheets

PHASED ARRAY ULTRASONIC NDT SYSTEM FOR TUBES AND PIPES

FIELD OF THE INVENTION

The invention relates to the non-destructive testing of tubes and pipes. In particular, it relates to the detection of longitudinal, transverse and oblique defects in tube walls using a phased array ultrasonic system.

BACKGROUND OF THE INVENTION

A new paradigm was defined in the field of non-destructive testing (NDT) with the introduction of phased array (PA) multi-element ultrasonic technology to upgrade the performance of conventional ultrasonic single-element probe systems. A general description of how phased array technology can be adapted to NDT systems is given in U.S. Pat. No. 5,563,346 with recent examples of applications for the inspection of spherically-bounded materials and turbine blades described in U.S. Pat. Nos. 6,279,397 and 6,082,198 respectively.

Another application is that of the inspection of tubes during production. Here, the "virtual rotation" of ultrasonic beams emitted by PA probes means that the probes themselves do not have to move as a tube being inspected passes through an inspection station. For a non-rotating tube, it is necessary to place PA probes at positions that cover the entire circumference of the tube.

Further advantages result when inspecting tubes or similar pieces (e.g., pipes, rods) using a PA ultrasonic NDT inspection system compared to conventional ultrasonic single-element probe systems. Little maintenance is required because such systems are robust with a relatively simple mechanical design, and what maintenance that is required is straightforward and structured for easy and quick implementation. Further, PA technology permits stationary, multi-element probes to thoroughly inspect a moving tube during manufacture with greater flexibility than conventional designs permit.

Such computer-controlled systems can be reliably and rapidly adapted to meet the requirements of various types and sizes of tubes by simply selecting electronically the software that corresponds to a new tube diameter and wall thickness to be inspected. The parameters affected would include the identification of specific piezoelectric elements in each probe for the formation of each beam, the number of beams per probe and the beam angle of incidence with respect to the outer surface of the tube. Further, the focus point of the PA ultrasonic beams can be adjusted electronically to be closer to the suspected location of defects in the tube walls for a given configuration. This is not possible with single-element probes.

PA technology has the important capability of readily detecting a wide range of defects having longitudinal, transverse and oblique orientations. This occurs because PA probes can electronically scan a much wider inspection zone than single-element probes are able to do. Previous work with single-element ultrasonic probes to broaden the inspection zone of such single-element probes is described in U.S. Pat. Nos. 4,718,277, 5,228,343, 5,473,943 and 5,485,751. It involves grouping single-element probes in clusters wherein the centerlines of the elements of such probes are angled relative to one another such that the beams they emit intersect at a predetermined position in the tube or pipe under inspection. Such single-element probe clusters, however, lack flexibility and the capacity to effect comprehensive inspections for oblique defects precisely because the ultrasonic beams are directed along the only a few discrete angles with respect to the inspected region.

Phased array prior art at R/D Tech Inc. in Québec City, Canada has been based upon a series of phased array probes that entirely encircle a tube, the multiple elements in each probe being angled as if lying on a conic surface with an included conic apex angle of, for example, 135 degrees. In such applications the inspected tube, while passing longitudinally through the ring of piezoelectric elements along the conic axis of the conic array of probes, has its surface analyzed for defects that are principally transverse or perpendicular to the longitudinal axis of the tube. In such systems each individual phased array beam emitted by a given probe enters the tube wall at a separate entry point. Thus a given portion of the tube wall is not inspected from multiple bearing angles originating from a single probe.

The objects of the invention are, therefore, to improve the way in which tubes are inspected during manufacture by being able to detect defects in a nearly continuous range of multiple orientations (e.g. longitudinal, transverse and oblique) in the wall of a tube; and by allowing the same system, with only minor adjustments (if any), to inspect a range of tube diameters and wall thickness for a given tube material and manufacturing process, or in tubes of differing materials and involving differing manufacturing processes.

The invention in its general form will first be described, and then its implementation in terms of specific embodiments will be detailed with reference to the drawings following hereafter. These embodiments are intended to demonstrate the principle of the invention, and the manner of its implementation. The invention in its broadest and more specific forms will then be further described, and defined, in each of the individual claims which conclude this Specification.

SUMMARY OF THE INVENTION

According to the invention in one aspect, a method of non-destructive testing for defects in the wall of tubes or pipes to be inspected is based upon a phased array (PA) ultrasonic probe system. The inspected tube may be rotated continuously while it is moving past an inspection station or the inspection station may be moved with respect to the tube. At the inspection station a plurality of PA beams from each of one or more probes are directed into an entry zone in the form of a spot on the outer surface of the tube wall. The position of the entry zone is fixed with respect to the probes. Said beams arrive at the entry zone with a fixed angle of incidence but from a range of bearing angles along conically oriented paths. Thus, the beams enter an inspection volume within the wall of the tube below the entry zone at a constant inspection angle. Defects within the inspection volume are detected by sensing reflected ultrasonic pulses created by such defects. Sensing may be effected by a circularly deployed array of dual-purpose emitter/receptor piezoelectric elements operating in either a pulse/echo or pitch/catch mode, or by dedicated emitters and receptors.

The invention is directed to a PA ultrasonic probe system that will detect reflecting longitudinal, transverse and oblique defects in the entire three-dimensional volume of the wall of a tube while the tube is moving with both longitudinal and rotational motion with respect to an inspection station. This can also be achieved, for example, by having the tube only rotate and the inspection system moving longitudinally with respect to the tube. By "reflecting defects" is meant defects that reflect sound waves either back to the source of such waves or laterally to other sensors.

As a preferred arrangement, a constant inspection angle (i.e., the angle of refraction of the beams in the tube wall) is pre-selected such that it meets the requirements of the inspection. These requirements depend principally on the tube material and the method of tube manufacture and establish an inspection angle that is most likely to detect anticipated defects. Since the inspection angle is constant, it follows that the angle of incidence at the entry zone for the ultrasonic beams emitted by the PA probes will also be predefined and constant.

The conically oriented PA beams are preferably generated by an arc of ultrasonic emitter/receptor elements mounted on a common, conic support surface, each of the elements having an emission face that is positioned to lie on the surface of an imaginary cone in space having a conic axis that is substantially normal to the longitudinal axis of the tube and which passes through the entry zone. The arc is preferably a circular arc. A set of elements occupying a sector portion, or all, of the circle constitutes a "probe". One or more probes may be contained within a module that also contains an acoustic coupling fluid.

Each PA beam is formed by the emission of synchronized ultrasonic waves from a sub-set or group of elements positioned within the arc of a probe. Such sound waves are synchronized to provide, for each respective PA beam, a focal point that is located within the inspection volume that corresponds to the entry zone. The total span of arc or arcs employed is preferably sufficient to ensure the detection of reflections arising from defects within the tube wall that are oriented obliquely within the three-dimensional inspection volume of the tube wall, as well as those oriented longitudinally or transversely. The detection mode of the probe or probes can be either pulse/echo or pitch/catch.

The PA probes are configured, according to one embodiment of the invention, in the form of conical sections with discreet elements side-by-side in a single, 1-dimensional, curved continuum for each probe provided by a conical supporting surface. The cone angle of the sections is a function of the predefined angle of incidence for the ultrasonic beams, which are emitted normally to the face of the probe elements, and are directed to strike the outer surface of the tube under inspection. Since the PA beams are preferably so formed as to strike said outer surface of the tube over a fairly small entry zone, tubes of varying geometries can be inspected using the same inspection set-up. This implies that the distance between the probe faces and the outer diameter of the tube is almost constant, being affected only slightly by the curvature of the various tube sizes. Any such small change in this distance is accommodated using mechanical "boots", containing or made of acoustic coupling fluid or material, that are adapted to fit tubes of different outer diameters.

Although all the beams must strike the tube in the entry zone, the distance between the probe face and the entry zone is generally not the focal length of the beams. Rather, the focal point of the PA beams is adjusted to be as close as possible to the suspected location of defects within the inspection volume so that very small defects can be detected. The optimum beam configuration is calculated using software in the control system to control the phased array probe elements to place the focal points as near as possible to locations most likely to have a defect.

The preferred angle subtended by each probe (also known as the "optical aperture") depends on the anticipated orientation of defects in the volume to be inspected (e.g., defects having longitudinal, transverse and oblique orientations or only a limited combination of these defects). The larger the optical aperture, the wider the range of defects that can be detected. Most defect orientations could be detected with an optical aperture of 360 degrees.

One embodiment of the invention has two mirror-image probes that occupy sectors of a circle located, facing each other, over the tube for providing clockwise and counter-clockwise inspections within the tube wall, viewed in cross-section. This allows detection of longitudinal and obliquely oriented defects in the volume of the tube wall. Alternately, the two mirror image probes, or two additional mirror image probes, may be so oriented with respect to the tube to conduct forward and backward inspections for transverse defects, again including obliques, in the volume of the tube wall.

As already described, the ultrasonic beams emitted by the PA probes preferably strike the entry zone on the outer surface of the tube under inspection at the same angle of incidence. In addition, according to the invention, each beam strikes the entry zone from a different direction (i.e., over a range of bearings) around a line normal to the tube at the entry zone. The range of bearings depends on the optical aperture of the probe; this could be 360 degrees for a fully conical probe. Only PA probes having a conical shape, as described above, are capable of doing this.

The preferred number of beams are selected to match the inspection parameters (anticipated orientation of defects, size of tube, speed of tube passing the inspection station, and the number of inspection modules). The conical shape of the probe allows all of the beams to be readily directed to the same entry zone. A preferred configuration effects inspection of a sample volume with three beams originating from each of two mirror image probes. The high sweep rate of the probes (approximately 15,000 beams/s) is such that the movement of the tube and the entry zone can be neglected for the short period of time it takes for the beams from one sweep to strike it. The rate of sampling for purposes of inspection should be sufficiently high so as to ensure that the entire volume of material in the inspection volume within the tube wall is exposed to PA beams arriving from all of the directions or orientations made available by the probes. In this way, the three-dimensional volume of the tube wall that corresponds to the entry zone during that short time can be inspected for the presence of any longitudinal, transverse or oblique defects, as anticipated by the inspection set-up.

In the next instant, after the tube has moved slightly to expose an adjacent small area of its outer surface as the entry zone, the process is repeated. Thus, as the tube passes through the inspection station, each point on its outer surface momentarily becomes the entry zone. Hence, as the tube advances past the inspection station, a spiral path of inspected tube wall will have passed through an active entry zone. If the tube is advanced at a sufficiently slow rate, this spiral path can cover the entire wall of the tube. Alternately, if the tube is advanced at a higher rate, multiple inspection stations may be progressively deployed along the path of the tube to provide a series of inter-entwined spiral paths of inspected tube wall that include the entire wall of the tube. In this way, complete inspection of the prescribed three-dimensional volume of the tube wall is effected.

In the embodiment of the invention described above an inspection system may consist of one or more pairs of mirror-image probes, each pair contained in a single inspection module. In such a system one pair of probes in a first module may be dedicated to detecting longitudinal defects (including obliques) and a second inspection module may detect transverse defects (also including obliques). Depending on the size of the tube and the speed at which it passes through the inspection station, several identical pairs of inspection modules may be required to detect all of the defects in the three-dimensional volume of the tube wall under inspection. These embodiments are alternates to a single probe having a 360 degree conical section which may replace the pair or pairs of probes with conical sections of lesser span or optical aperture.

Another embodiment of the invention consists of one or more modules each containing a mirror-image pair of PA probes to detect only longitudinal and oblique defects. In this embodiment, transverse defects only (i.e., not including obliques) are detected by two conventional single-element probes, one looking forward and the other backwards along the tube. This embodiment may be further embellished by the addition of one or more single-element probes to simultaneously verify, for example, tube wall thickness or to detect delamination.

In the embodiments described thus far, a PA ultrasonic probe system with a predefined angle of incidence and fixed entry zone is capable of inspecting a range of tube sizes and wall thickness. The only modification that might be required by different tube diameters is changing of the previously-mentioned boot at the interface between the bottom of each module and the outer surface of the tube to ensure the stability of the interface. Such a system may consist of one or more modules.

Should circumstances dictate, a different predefined angle of incidence may require design changes to cater for the altered dimensions of, for example, the conical probe sections and the distance between the probe faces and the outer diameter of the tube. Once built, however, this new system would also be capable of inspecting a range of tube sizes and wall thicknesses without further modification, as described above.

In an additional embodiment, the restriction of having to redesign the module for each predefined inspection angle is overcome by using a 2-dimensional array of ultrasonic probes. In these probes, there are both elements discreetly placed side-by-side lengthwise and around the circumferential surface of the imaginary cone to provide the electronic axis that forms the beams; and elements discreetly placed side-by-side along the inclined surface of the imaginary cone, that allow changes in the direction of the beam, thereby controlling the angle of incidence of the beam with respect to the probe surface. This compares to the 1-dimensional probes of the earlier embodiments that have an electronic axis of variable length but only a single fixed directional axis. Using PA beam steering techniques, the 2-dimensional probes form beams that may be tilted with respect to beams formed with 1-dimensional probes, thereby allowing the angle of incidence to be altered without having to redesign the module.

The foregoing summarizes the principal features of the invention and some of its optional aspects. The invention may be further understood by the description of the preferred embodiments, in conjunction with the drawings, which now follow.

DETAILED DESCRIPTION OF THE PREFERRED EMBODIMENT

The invention describes a phased array (PA) ultrasonic system for detecting reflecting defects having multiple orientations (i.e., longitudinal, transverse and oblique) located throughout the entire three-dimensional volume of a tube wall as the tube passes through a non-destructive testing (NDT) station.

Figure 1:
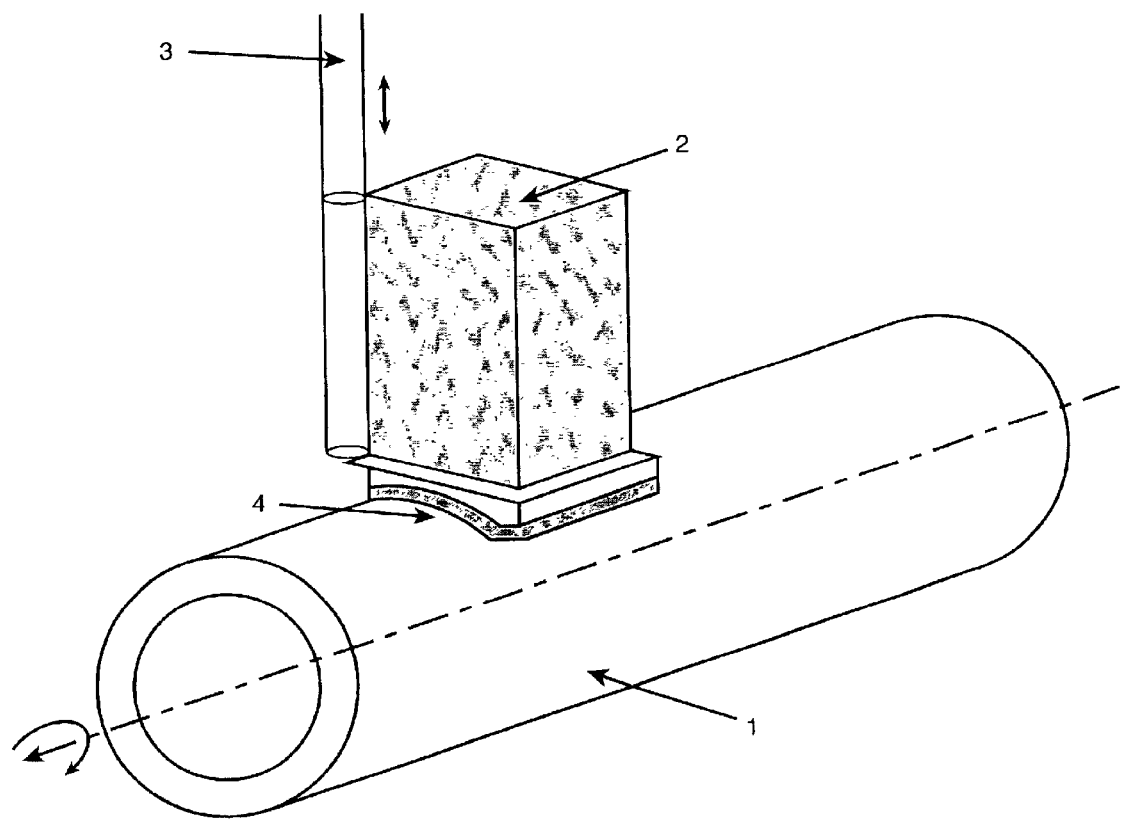
FIG. 1—General physical relationship between phased array ultrasonic module and tube under inspection.

FIG. 1 shows the relative disposition of ultrasonic PA module 2 with respect to tube 1 under inspection. When inspection is underway, positioning mechanism 3 lowers module 2 until it comes into contact with acoustically transparent boot 4, a mechanical device well known in the field of NDT, which forms an interface between tube 1 and module 2. Water then flows around the boot to fill any small spaces remaining between tube 1 and module 2. Module 2 is free to move up and down as well as sideways in rhythm with any eccentric fluctuations tube 1 may have as it passes through the inspection station.

During inspection, tube 1 rotates and moves longitudinally with respect to module 2. Module 2 may be held stationary except to accommodate tube fluctuations as described above. There is no impediment, however, to only rotating the tube (i.e., no longitudinal movement) and sliding the module longitudinally over it using a suitable mechanical control mechanism, should that be more convenient for a particular design set-up.

Figure 2:
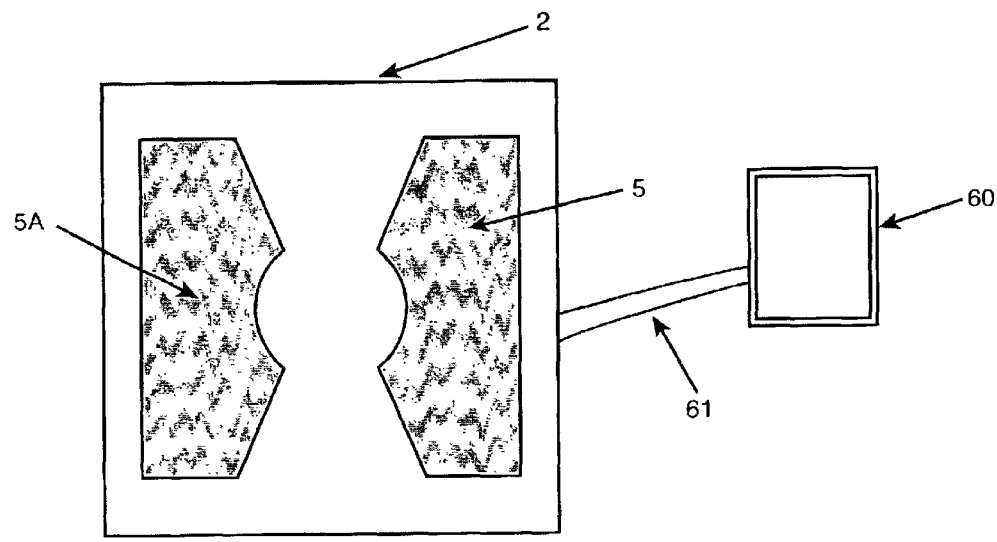
FIG. 2—Top view of phased array ultrasonic module with top cover removed, including associated computer controller/data acquisition system.

As illustrated in FIG. 2 in a top view, PA ultrasonic module 2 contains two opposing mirror-image PA ultrasonic probe assemblies 5 and 5A that each span a 60 degree sector of a circle (i.e., the optical aperture). Also shown in FIG. 2 are associated computer/data control and acquisition system 60 and electronic cabling 61 connecting it to module 2. When inspecting tubes, such probe assemblies are preferably required in mirror pairs so that complementary forward and backward measurements for transverse defects, or complementary clockwise and counterclockwise transverse measurements, can be made.

Figure 3A:
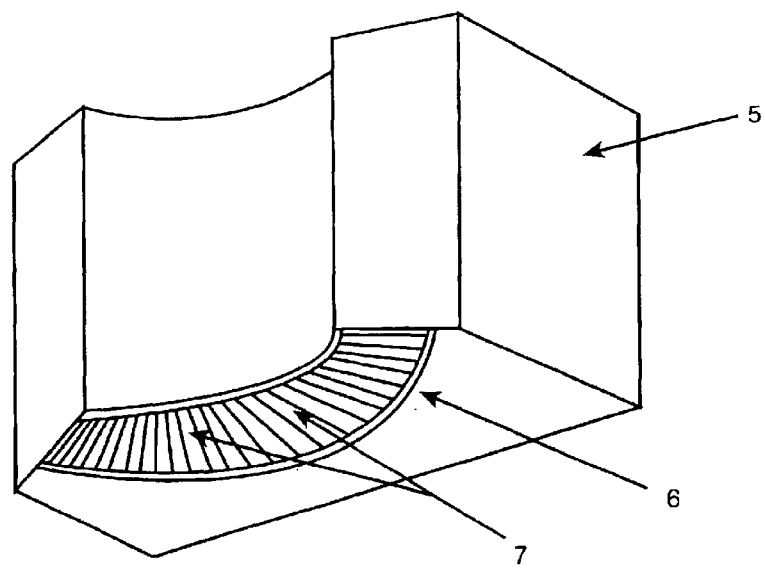
FIG. 3A—Three-dimensional view of phased array ultrasonic conical probe segment.
Figure 3B:
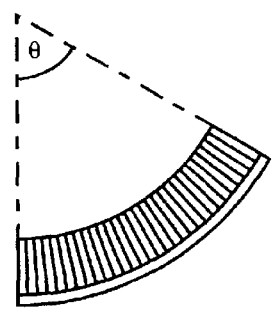
FIG. 3B—Plan view of phased array ultrasonic conical probe segment subtending an angle of 60 degrees.

FIG. 3A shows details of one of the probe assemblies of which the key component is PA ultrasonic probe 6 in the form of a conical section containing 64 ultrasonic emitter/receptor elements 7, (not all elements 7 are depicted in FIG. 3A). As shown, these elements 7 are all discreet and side-by-side in a single continuum for each probe and, as such, may be considered as 1-dimensional. As illustrated in FIG. 3B, the conical section subtends a sector angle of θ (the optical aperture), where θ=60 degrees in the described preferred embodiment. This optical aperture θ, however, is arbitrary and can be increased or decreased at will to meet design requirements. The degree of obliquity that can be detected from the longitudinal or transverse directions depends on the optical aperture θ. It is determined in advance by anticipating the maximum extent of projected obliquity due to the manufacturing process and the tube material and size. The larger the optical aperture θ, the greater the degree of obliquity that will be detected.

In the preferred embodiment, each of the 64 piezoelectric ultrasonic elements 7 in probe 6 have a width of 1.2 mm, a length of 19 mm and an operating frequency of 2.25 MHz. The number and design of ultrasonic elements 7 is also arbitrary and can be changed at will depending on performance requirements. The electronics, multiplexing and software 60 and 61 that control the operation of elements 7 of probe 6 through controllers 60, as pictorially shown in FIG. 2, are well known in the general field of phased array probes and can be purchased from R/D Tech Inc. of Québec City, Canada.

Figure 4:
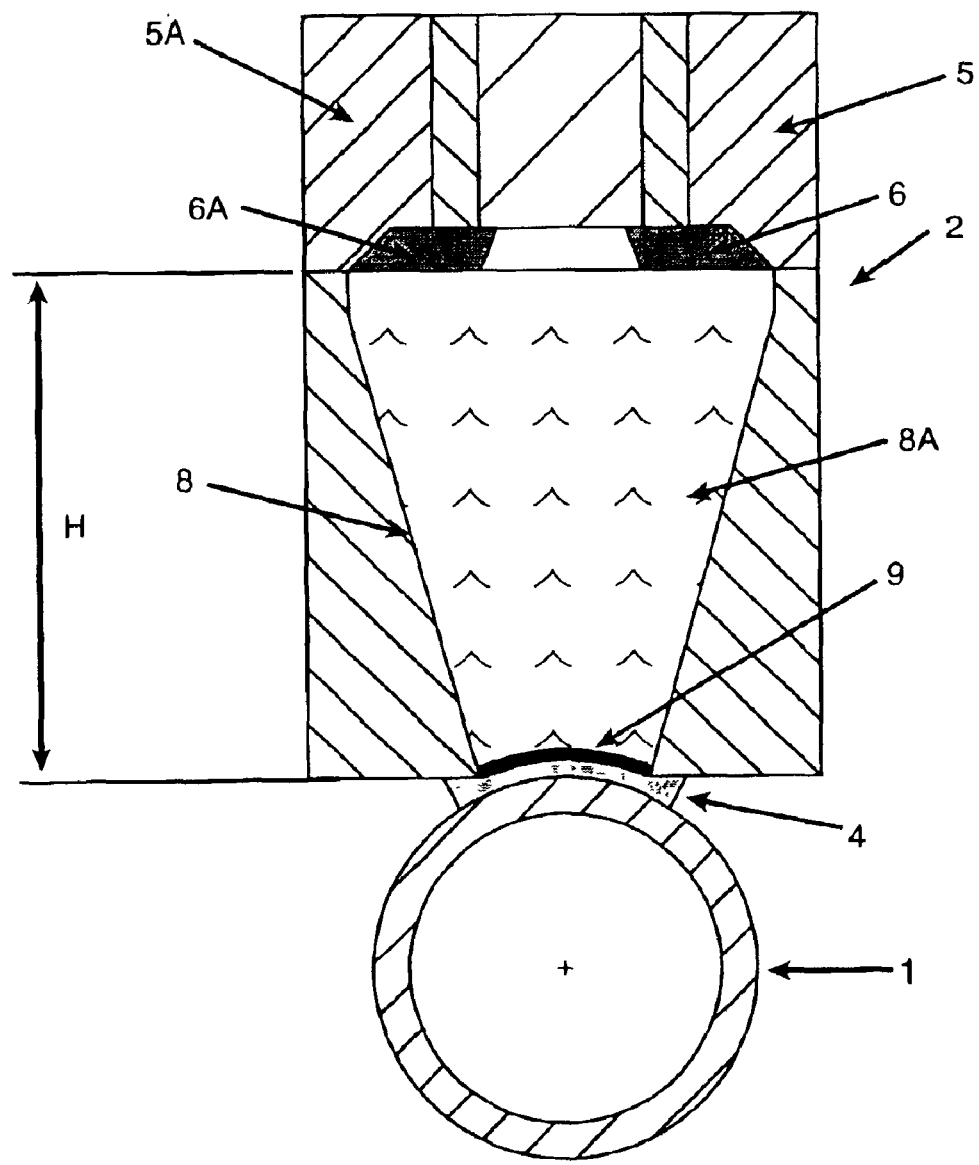
FIG. 4—End view cross-section of phased array ultrasonic module.

The internal design of module 2 is shown in cross section in FIG. 4. Probe assemblies 5 and 5A, respectively containing conical probe sections 6 and 6A, are located at the top of truncated coupling column 8, which is completely filled with acoustic coupling fluid 8A such that there is no gap between probe sections 6 and 6A and coupling fluid 8A. The bottom of truncated coupling column 8 is normally sealed by membrane 9, which may be flat or be sufficiently flexible to take up a curvature similar to that of tube 1. The letter "H" shows the height of the coupling fluid. Boot 4 is placed between membrane 9 and tube 1 to ensure a continuous and integral interface. Small spaces left after insertion of the boot 4 are filled by externally flowing water or some other coupling fluid during inspection. Depending on the tube outer diameter, boot 4 can be changed to achieve a better fit.

Figure 5:
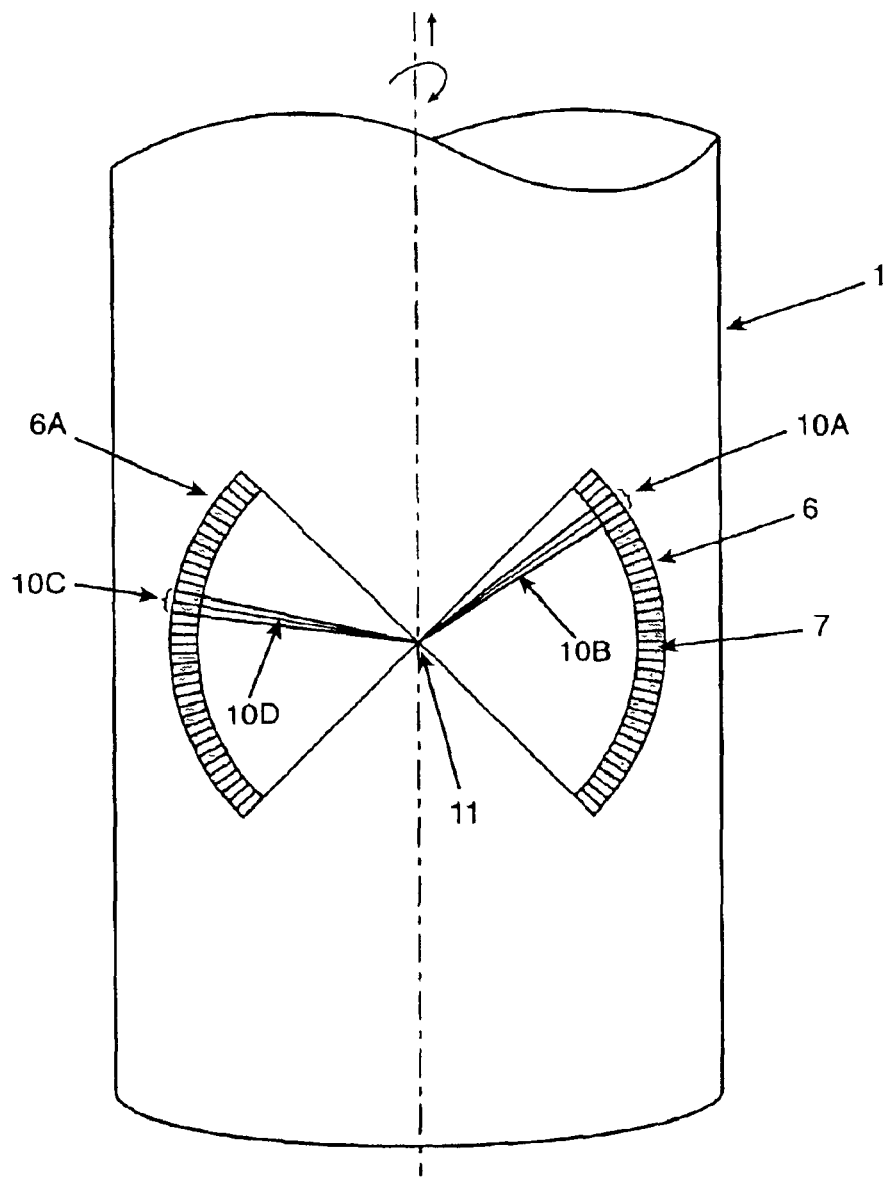
FIG. 5—Top view schematic representation of a pair of opposing phased array ultrasonic conical probe segments showing beam orientation.

The manner in which the phased array beams enter tube 1 in order to detect the defects within their 60 degree subtended sector angle is illustrated in FIG. 5, which is a top view looking downwards through PA ultrasonic probes 6 and 6A with tube 1 below them. Since the method of operation of probes 6 and 6A is identical, except that one may rotate its beams clockwise and the other counterclockwise, the following description will be limited to probe 6. Beams are formed by groups of ultrasonic piezoelectric elements 7, preferably contiguous, acting in virtual unison; the number of elements per group being arbitrary, depending on the overall design of the system and the application. The preferred embodiment described herein has eight elements 7 per group (not all elements 7 are depicted in FIG. 5). Such groups are typically identified by the number 10A in probe 6 and 10C in probe 6A in FIG. 5. When the elements 7 in groups 10A and 10C are triggered, beams 10B and 10D are respectively formed. The method of detection in the preferred embodiment is pulse/echo, but pitch/catch could also be used.

Figure 6:
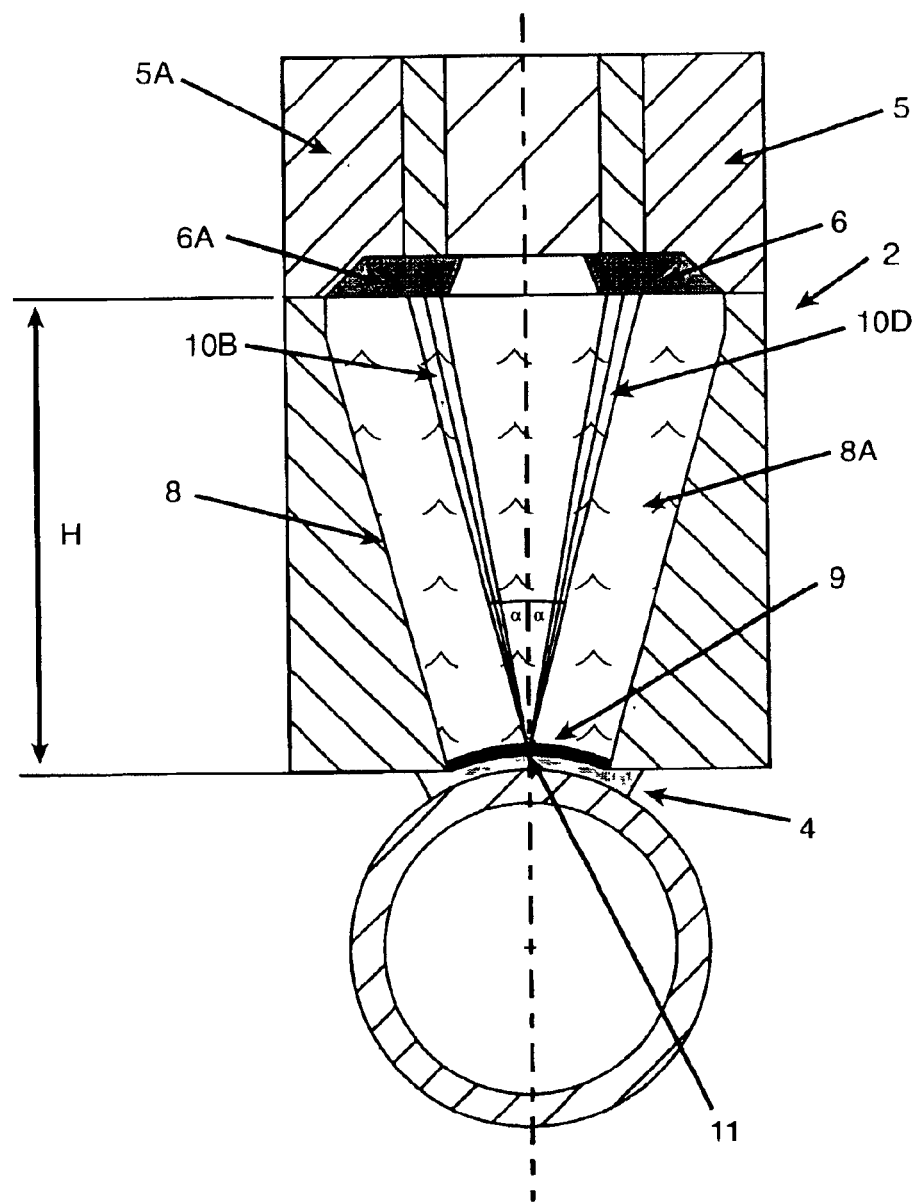
FIG. 6—End view cross-section of phased array ultrasonic module showing beam orientation.

The design of PA ultrasonic module 2 is such that all beams from probe 6 (e.g., beam 10B), as well as all beams from probe 6A (e.g., beam 10D), coincide and strike the outer diameter of the tube at the same point or region 11, known as the "entry zone" 11, as illustrated from the top in FIG. 5 and from the end in FIG. 6.

Beams 10B and 10D, as well as all other beams emitted from probes 6 and 6A, generally do not arrive at entry zone 11 at their focal point. Better detection of defects, particularly very small defects, is possible if the focal points of the ultrasonic beams is within the inspection volume inside the tube wall, as close to the location of anticipated defects as possible, as controlled by software integrated into the system. The focal length of the beams, therefore, is a function of the type of defects anticipated and the geometry of the tube under inspection, and it is predetermined based on these considerations.

Figure 6A:
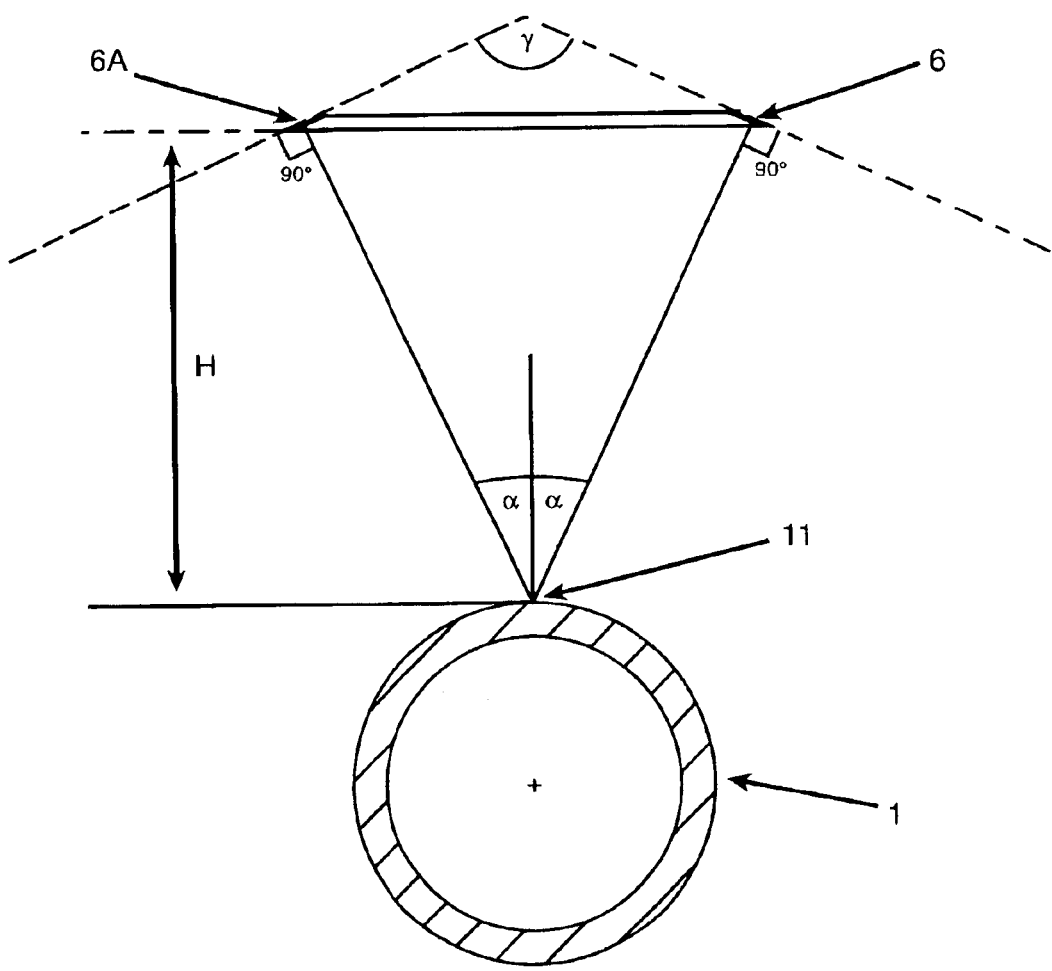
FIG. 6A—End view cross section of phased array probe cone showing cone angle.

The geometry of PA ultrasonic module 2 depends fundamentally on the type of defect that is to be detected in the tube. The type of defect, which is a function of such factors as the material and method of manufacture of the tube, dictates the angle of refraction of the inspection beams for optimum detection of such defects. From this information, the required angle of incidence α of the beams can be readily calculated and this leads directly to the cone angle γ of the probe and height H of the acoustic coupling fluid 8A, as illustrated geometrically in FIG. 6A.

For the preferred embodiment described herein, α=17 degrees, H=90 mm and γ=73 degrees. As can be seen in 146 FIG. 6A, this value of cone angle γ is dependent on the ultrasonic beam emanating at a right angle from the conical surface of the probe.

Using eight contiguous emitter/receptor elements 7 per PA beam, the 64 elements 7 of probe 6 can be grouped to form up to eight beams without overlapping pulsing of elements, or up to 57 beams with overlapping pulsing of elements. The actual number of beams for a given inspection depends on the requirements of the inspection. For the preferred embodiment, only three beams are utilized per tube type due to the high speed at which the tube passes the inspection station (2 m/s). The groups of eight elements 7 per beam are changed, however, for different tube types where the anticipated obliquity of the defects is different, such obliquity being a function of the method of manufacture and tube size.

Although all beams formed by these groups strike the tube at entry zone 11, their focal points are adjusted to be as close as possible to the suspected location of defects in the inspection volume in the tube wall corresponding to the entry zone. All beams have the same incident angle α with respect to tube 1. Since the beams are formed very rapidly (~15,000/s depending on acoustic limitations), they will enter entry zone 11 before the tube can move appreciably in either a longitudinal or rotational direction. The size of entry zone 11 can vary, but is typically in the range of 5–10 mm across, but may lie in a range from 1 to 30 mm. For the preferred embodiment it is 9 mm wide. As tube 1 moves past entry zone 11, all points on its surface momentarily become part of entry zone 11 during which time they are bombarded with beams all having the same angle of incidence α.

Figure 7:
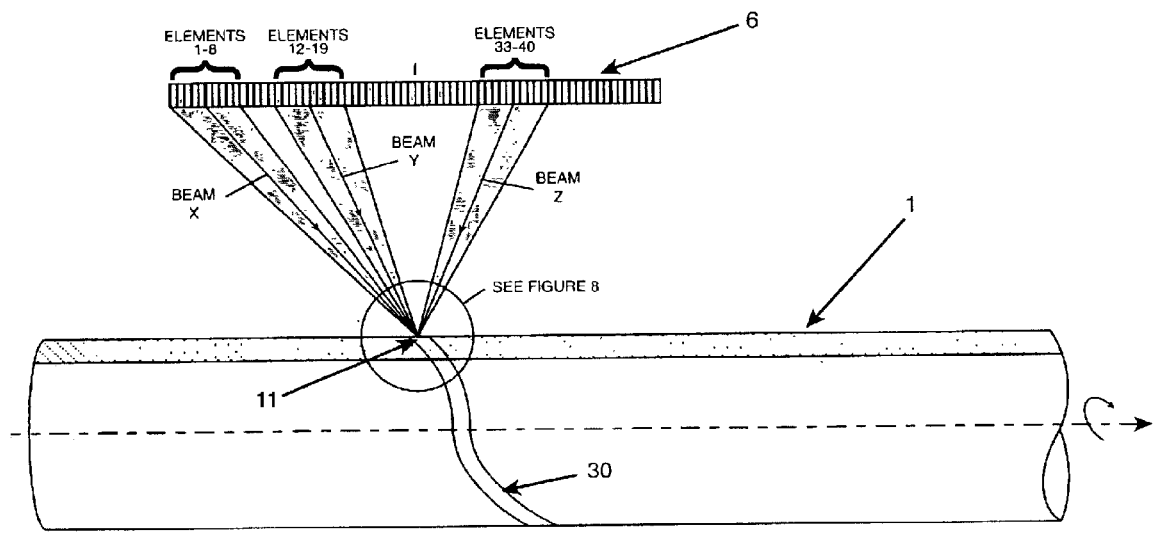
FIG. 7 Side view of phased array ultrasonic probe showing formation of incident beams.
Figure 8:
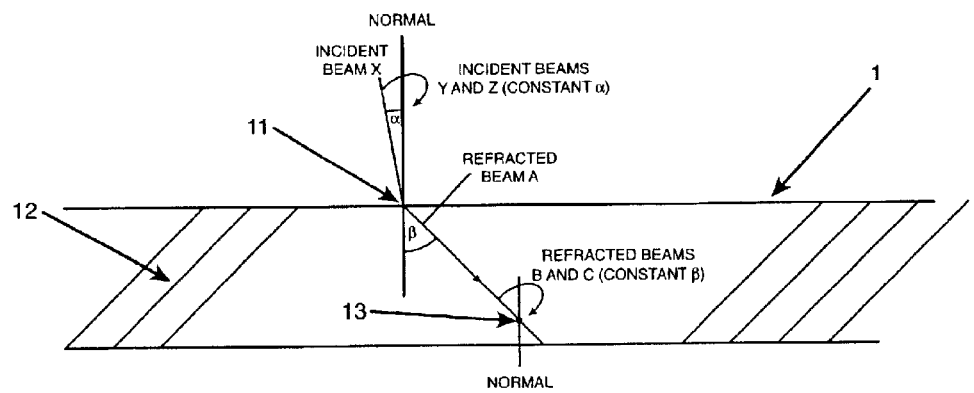
FIG. 8 Cross-section of tube wall showing incident and refracted beams.

As indicated above, in the preferred embodiment described herein, three groups of eight emitter/receptor elements 7 each were considered sufficient to conduct the inspection. In FIG. 7, beams X, Y and Z, respectively formed by non-overlapping groups consisting of elements 1 to 8, 12–19 and 33–40, are shown entering tube 1 at entry zone 11. An enlargement of the area around entry zone 11 is given in FIG. 8. Here it can be seen that beam X strikes entry zone 11 at incident angle α from one direction and that beams Y and Z strike entry zone 11 at the same incident angle α, but from different directions. Each of beams X, Y and Z is refracted by the same amount, hence all three pass through tube wall 12 at refraction angle β (also known as the "inspection angle"). All points in tube wall 12, as exemplified by point 13 in FIG. 8, are inspected at angle β by beams X, Y and Z. In this way, every point in the tube wall being subtended by the 60 degree conical probe section (optical aperture) of the preferred embodiment is inspected by beams coming from three or more different directions within the aperture (i.e., from 0 degrees to 60 degrees). The only restriction on the number of beams to conduct an inspection are the requirements of the inspection.

Figure 9:
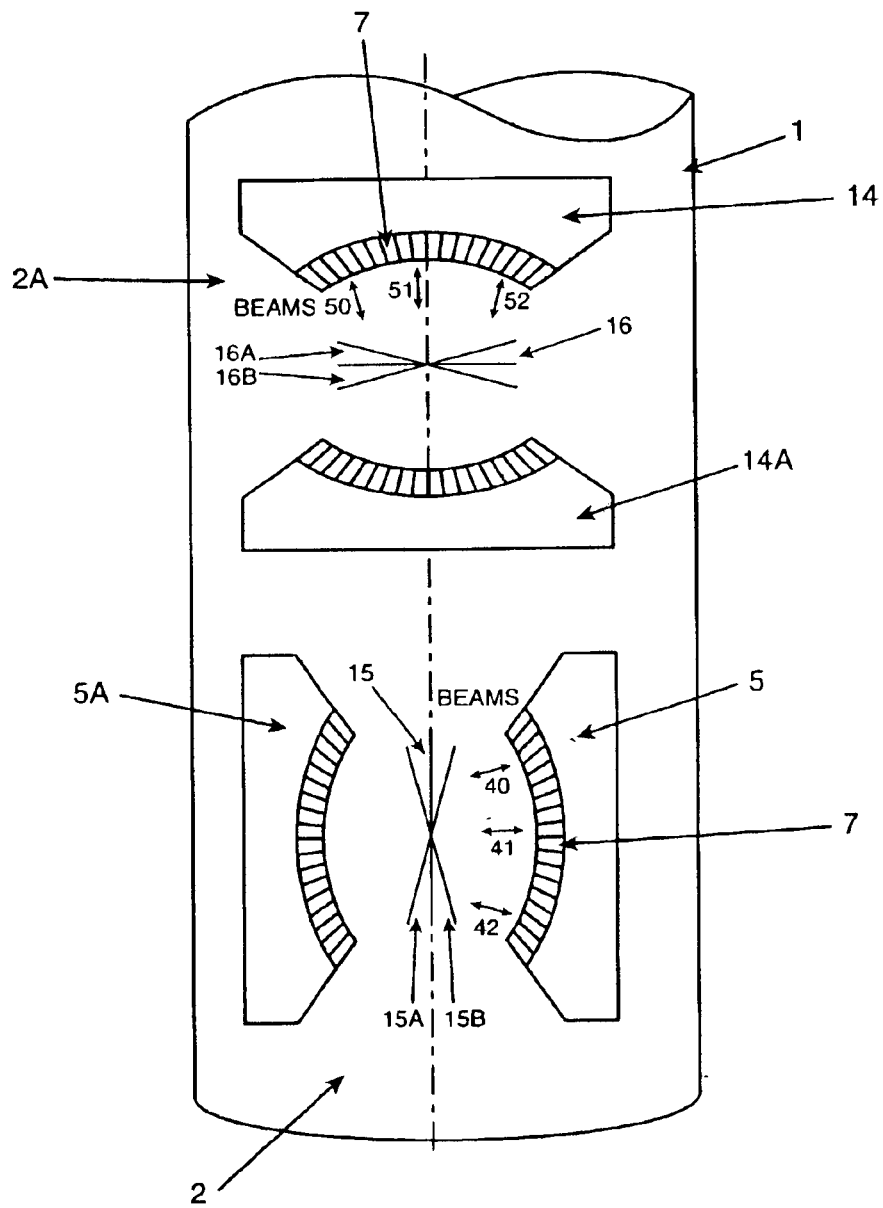
FIG. 9 Top view schematic representation of detection of longitudinal, transverse and oblique defects by two opposing pairs of phased array ultrasonic probes with the form of conical segments.

FIG. 9 further illustrates how reflecting longitudinal defects are detected in the zone of the tube wall under inspection. If longitudinal defect 15 and oblique defects 15A and 15B are to be detected, beams at or close to normal to them must strike them so that there is maximum reflection back to the corresponding emitter/receptor element 7. Hence, beam 41 emanating from probe 5 will detect longitudinal defect 15 at an angle of approximately 90 degrees, and beams 40 and 41 will respectively detect oblique defects 15B and 15A at angles of approximately 90 degrees. This occurs because the angle of incidence and directions of the beams have been pre-selected as a function of the anticipated degree of obliquity of the defects. Compared to conventional ultrasonic technology (i.e., single-element probes) PA technology yields a much higher resolution in the direction of defect orientation (the decrease in sensitivity is close to 1 db per degree of defect orientation out of alignment from the detecting direction). This results in a higher degree of accuracy in defect identification.

For certain types of tubes, this may be the only inspection required, but for others it may be desired to detect transverse and transverse oblique defects as well. To do this using the preferred embodiment described thus far, it would simply be necessary to add a second module 2A containing phased array mirror-image ultrasonic probe assemblies 14 and 14A aligned as shown in FIG. 9. In the same way as described above, beam 51 detects transverse defect 16 while beams 50 and 52 respectively detect oblique transverse defects 16B and 16A.

Figure 10:
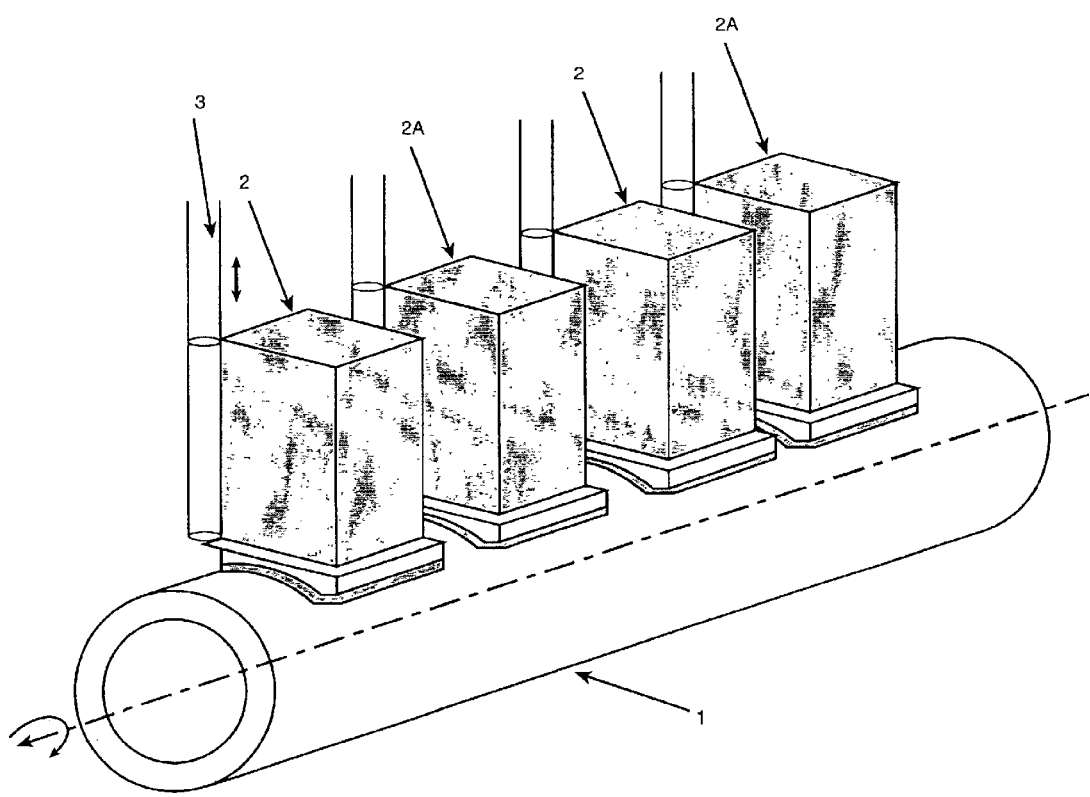
FIG. 10—Multiple phased array ultrasonic modules mounted on tube under inspection.

Thus, module 2 inspects for longitudinal defect 15 and oblique defects 15A and 15B; and module 2A inspects for transverse defect 16 and oblique defects 16A and 16B. How they could be positioned over the tube to be inspected is shown in FIG. 10. Additional modules or pairs of modules can be added if the longitudinal and rotational speeds of the tube so warrant. If module size is not a restraint, modules 2 and 2A for the detection of both longitudinal and transverse defects respectively could be combined in a single module, as could the other pairs of modules referred to above. The relative location of the modules is unimportant (i.e., they do not have to be in close proximity to one another).

FIG. 7 also shows spiral path 30 that is inspected by entry zone 11 during one rotation of tube 1 as tube 1 moves through the inspection station. If tube 1 is advanced at a sufficiently slow rate, spiral path 30 will cover the entire wall of the tube. Alternately, if the tube is advanced at a higher rate, multiple modules may be progressively deployed along the path of the tube, in the same way as illustrated in FIG. 10, to provide a series of inter-entwined spiral paths 30 of inspected tube wall that include the entire wall of the tube. In this way, complete inspection of the prescribed three-dimensional volume of the tube wall is effected.

Figure 11:
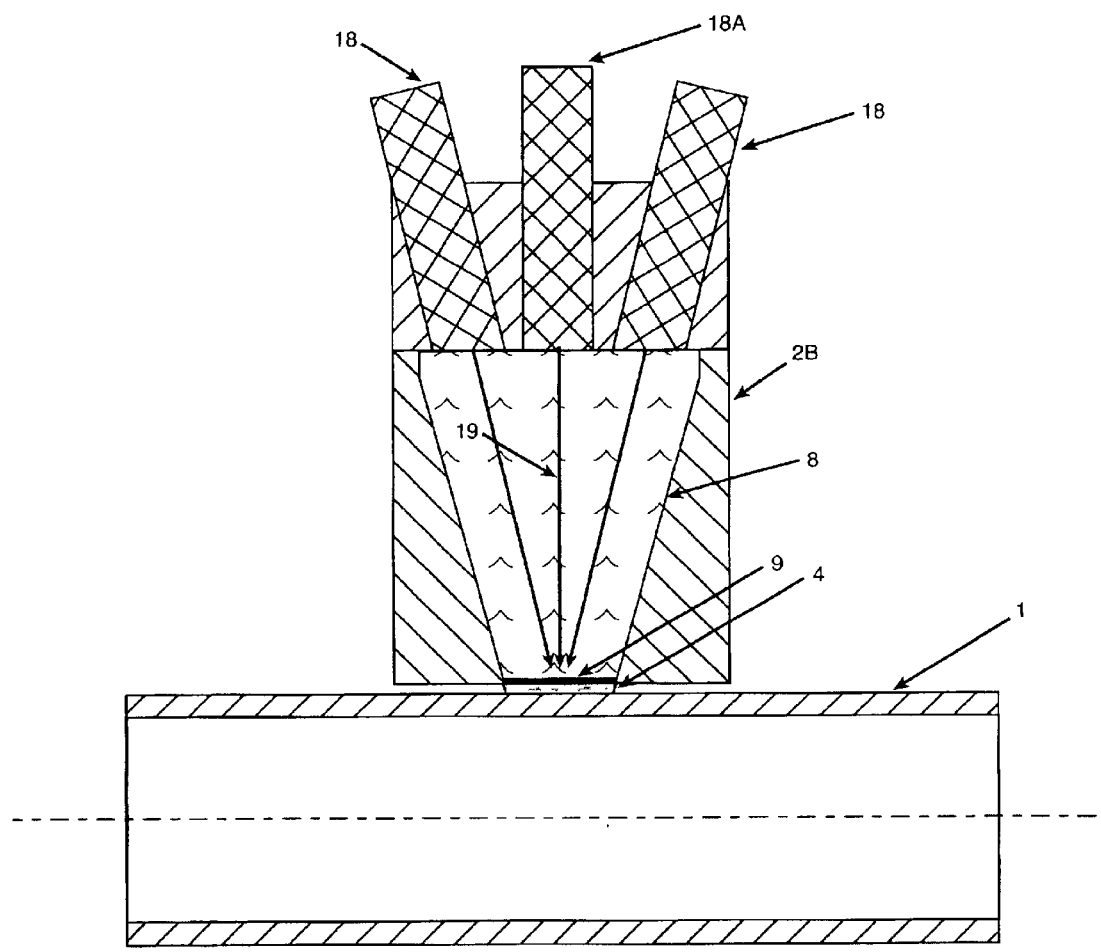
FIG. 11—Side view cross-section of module in the preferred embodiment showing one pair of ultrasonic PA probes and three conventional ultrasonic single-emitter probes.

The preferred embodiment is depicted in FIG. 11. It consists of module 2C, which contains only one pair of PA probes because the requirement is only for the detection of longitudinal and oblique defects. In addition, a pair of centrally located, conventional single-element probes 18 is used for the forward and backward detection of transverse defects (no obliques). The preferred embodiment also contains a third centrally positioned, conventional single-element probe 18A for the measurement of wall thickness and detection of delamination. Due to the high speed at which the tube passes the inspection station, there are four identical modules 2C in the preferred embodiment located over the tube in the same configuration as shown in FIG. 10 for modules 2A and 2B.

Figure 12:
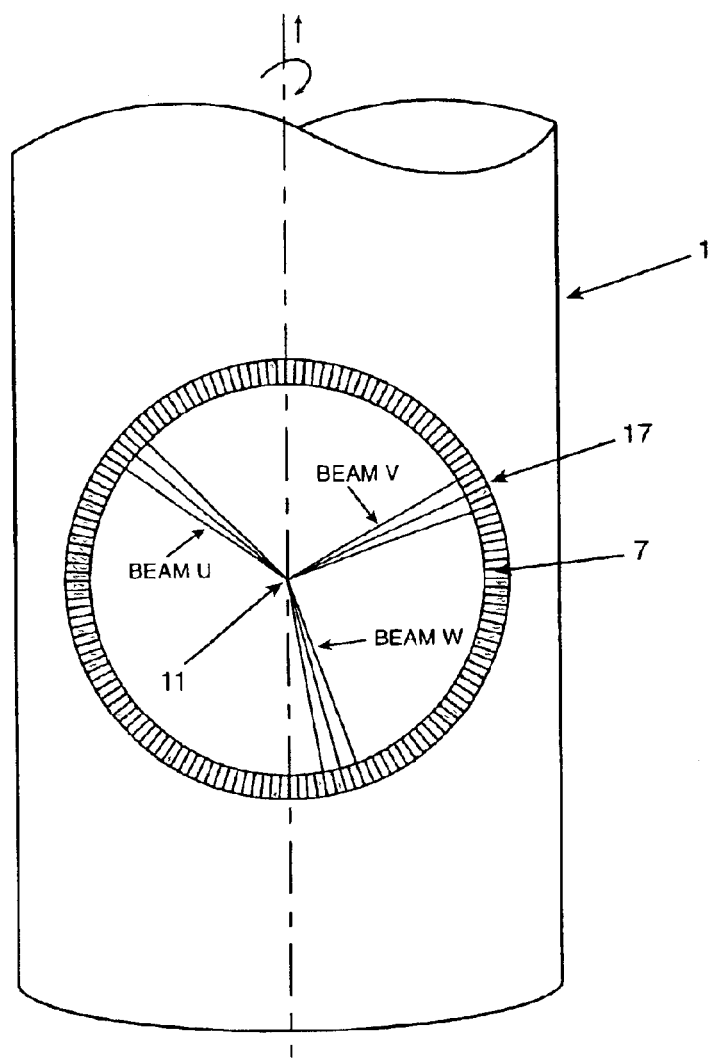
FIG. 12—Top view schematic representation of detection of longitudinal, transverse and oblique defects by a single 360 degree conical phased array ultrasonic probe.

Alternatively, as shown in FIG. 12, a full 360 degree conical PA ultrasonic probe 17 could be employed to detect defects in the tube regardless of their orientation. It would be made up of several hundred elements 7, which would be formed into many groups to produce beams. Three such beams U, V and W are shown, all striking the outer circumference of tube 1 at entry zone 11, as described above.

Figures 13A, 13B, 13C:
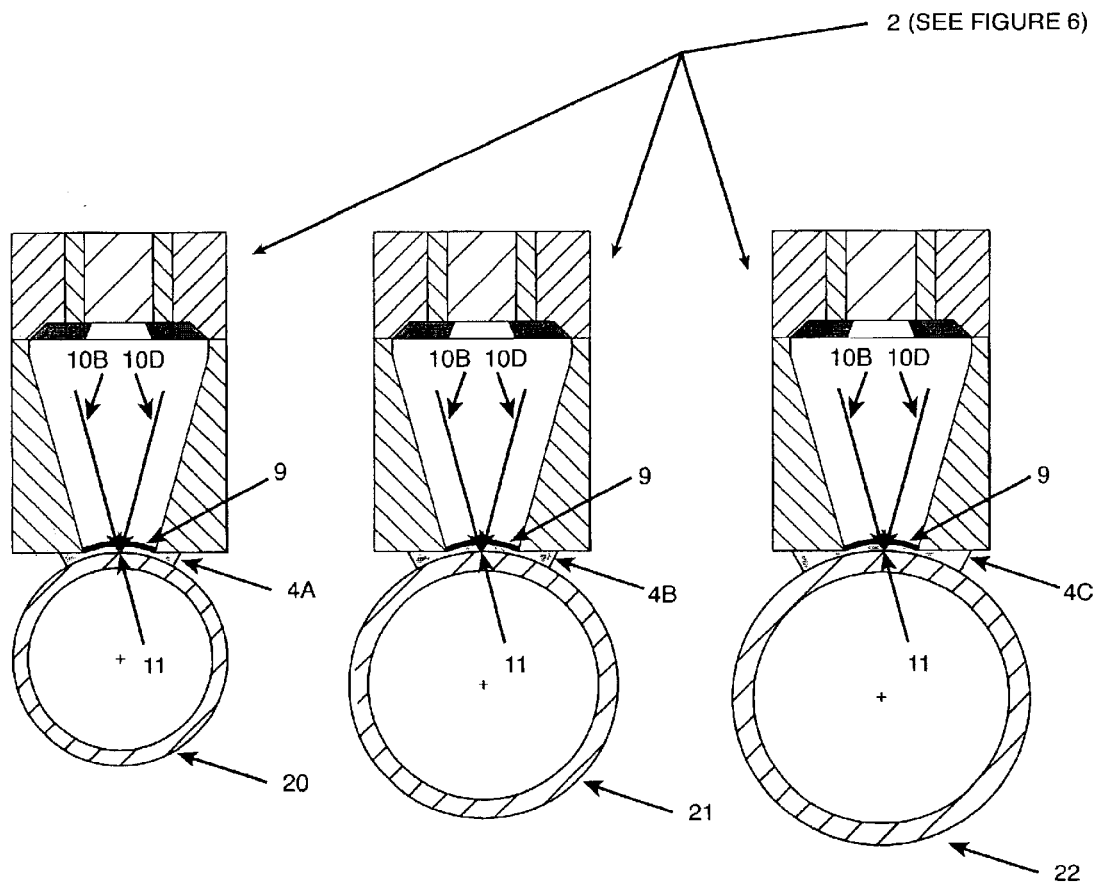
FIG. 13A—End view cross-section showing how a fixed phased array ultrasonic module design can detect longitudinal, transverse and oblique defects of a first pre-defined type for tubes of varying diameter: tube with small diameter and thin wall thickness.
FIG. 13B—End view cross-section showing how a fixed phased array ultrasonic module design can detect longitudinal, transverse and oblique defects of a first pre-defined type for tubes of varying diameter: tube with medium diameter and thick wall thickness.
FIG. 13C—End view cross-section showing how a fixed phased array ultrasonic module design can detect longitudinal, transverse and oblique defects of a first pre-defined type for tubes of varying diameter: tube with large diameter and medium wall thickness.

A single module design can be used for detecting pre-defined types of defects (i.e., for a predefined angle of incidence α) in a range of tube diameters and wall thickness. Under these circumstances, the conical aperture θ of the probe (see FIG. 3B), the cone angle γ of the probe (see FIG. 6A) and the height H of the coupling fluid (see FIG. 6) are fixed. As illustrated in FIG. 13A (tube 20 with small diameter and thin wall thickness), FIG. 13B (tube 21 with medium diameter and thick wall thickness and FIG. 13C (tube 22 with large diameter and medium wall thickness), the ultrasonic beams from the same phased array probe (e.g., beams 10B and 10D) all pass through entry zone 11, thereby all entering the tube to be inspected at the same point on the outer circumference regardless of tube diameter or wall thickness. Slightly differing boots 4A, 4B and 4C ensure a stable interface between the module and the tube.

Should a different type of defect be predefined, it would then be necessary to redesign the module (2' instead of 2 in FIG. 6). For example, a different tube material or a different method of manufacture would require a different inspection angle of refraction (β' instead of β in FIG. 8). Knowing this, the corresponding angle of incidence (α' instead of α in FIG. 6), the height of the coupling fluid (H' instead of H in FIG. 6) and the cone angle (γ' instead of γ in FIG. 6A) can be readily computed in the same way, as described above for the computation of α, H and γ. It may also be decided to modify the optical aperture for the phased array probe (θ' instead of θ in FIG. 3B). Once fabricated, module 21 can be used to inspect for the new predefined defects in tubes of varying diameters and wall thickness made from the new material and manufacturing process in the same way as illustrated in FIGS. 13A, 13B and 13C for module 2.

Figure 14A:
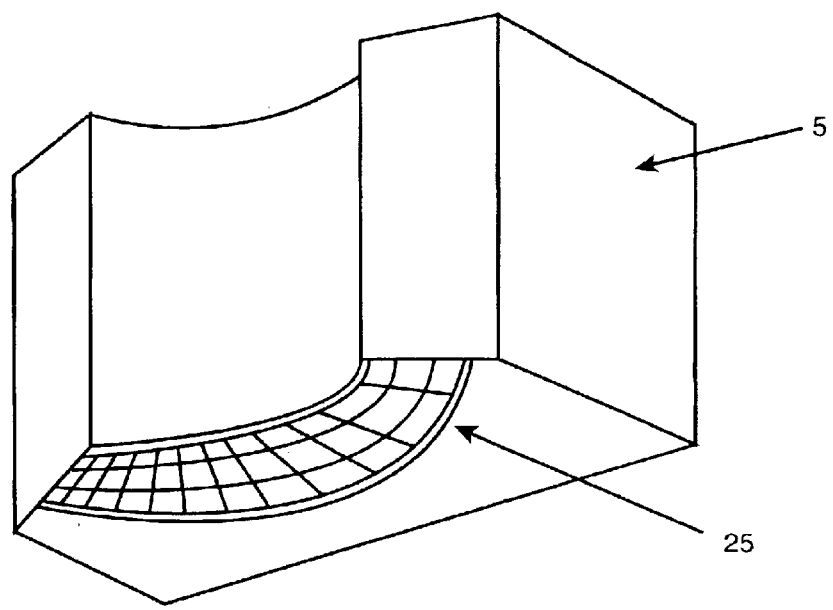
FIG. 14A—Three-dimensional view of 2-dimensional phased array ultrasonic probe.
Figure 14B:
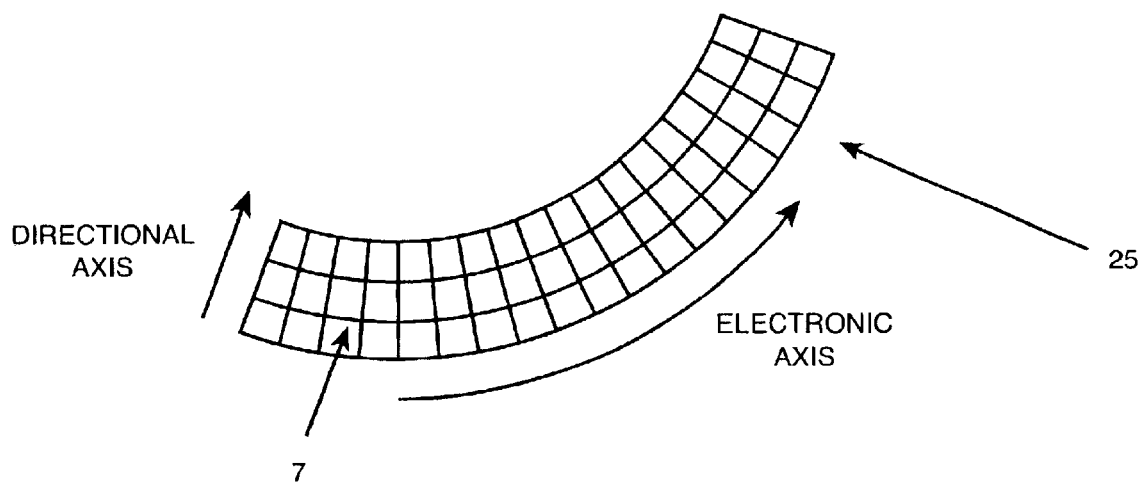
FIG. 14B—Sketch of 2-dimensional probe showing electronic and directional axes of probe in FIG. 14A.

The restriction of having to redesign the module for each predefined inspection angle can be overcome by using 2-dimensional ultrasonic probes. In the previously described embodiments, the elements 7 making up the PA probes are 1-dimensional in that they are all side-by-side in a single continuum for each probe (see description for FIG. 3A). That is, the only axis of freedom for placement of the beam focal point is this electronic axis, which the elements 7 define and which controls the formation of the beams. As illustrated in FIGS. 14A and 14B, a directional axis can be created for each probe, if additional elements 7 are added to give 2-dimensional probe 25 a depth of three elements 7 all along its arcuate span/electronic axis length. The number of additional rows of elements that provide the directional axis is optional.

By employing standard PA beam steering techniques, the acoustic beams can be adjusted along both axes, thereby permitting a variable inspection angle. In this way the angle of incidence α can be altered without having to redesign the module. Using this technique, the height H will not be exactly the same as in the 1-dimensional case (i.e., the entry zone will not lie exactly on the outer surface of the tube), but the design of the boot 4 can be adjusted to compensate for this without appreciable effect on the inspection capability.

The preferred embodiment described above has been built and repeatedly tested with great success for the inspection of tubes having outer diameters from 70 to 500 mm and wall thickness from 4 to 20 mm. In addition, using this system, tests have successfully located transverse oblique defects in very thin wall thickness (1 mm in tubes of 17 to 24 mm outer diameter).

CONCLUSION

The foregoing constitutes a description of specific embodiments showing how the invention may be applied and put into use. These embodiments are only exemplary. The invention in its broadest and more specific aspects is further described and defined in the claims, which now follow. These claims, and the language used therein, are to be understood in terms of the variants of the invention, which has been described. They are not to be restricted to such variants, but are to be read as covering the full scope of the invention as is implicit within the invention and the disclosure that has been provided herein.

What is claimed is:

1. A system for the non-destructive testing of tubes comprising one or more ultra-sonic modules each of said modules comprising:
   (1) one or mare ultrasonic probes comprising a plurality of phased array ultrasonic elements;
   (2) an acoustic coupling fluid contained within a column extending downwardly from the probe; and
   (3) a boot for effecting an interface between said module and a tube having a tube wall to be tested,
   wherein the ultrasonic elements are deployed in the shape of a conical section having an included cone angle with the elements positioned side-by-side in an arcuate array to provide a phased array probe, whereby a plurality of phased array beams maybe directed from each of said one or more probes into an entry zone on an outer surface of said tube wall, said beams arriving at the entry zone from a range of bearing angles along conically oriented paths.

2. The system in claim 1 wherein the beams emitted by each of said one or more probes all strike the entry zone with the same angle of incidence with respect to the outer surface of said tube.

3. The system in claim 1 wherein the modules each contain a pair of mirror-image probes.

4. The system in claim 3 wherein each of the pair of mirror-image probes provides three or more phased array beams directed from said respective probes into the entry zone.

5. The system in claim 4 wherein the plurality of phased array ultrasonic elements in each of the pair of mirror-image probes are deployed in a circular array that subtends substantially 60 degrees of a circle.

6. The system in claim 1 wherein said one or more of the modules further comprise one or more single-element ultrasonic probes.

7. The system in claim 1 where the plurality of phased array ultrasonic elements are a first series of ultrasonic elements and a further series of ultrasonic elements are deploy beside said first series to form a 2-dimensional array of ultrasonic elements.

8. A system for the non-destructive testing of a tube having a tube wall to detect the presence of defects within said wall, including one or more modules each comprising:
   (a) one or more ultrasonic phased array probes, each including a first plurality of ultrasonic elements;
   (b) means to supply electrical signals to the ultrasonic elements to cause said ultrasonic elements to emit ultrasonic, phased array beams that respectively form a focal point;
   (c) an acoustic coupling fluid contained within a column extending from said one or more probes to the foot of said column;
   (d) acoustic coupling means extending between the foot of said column and a portion of the tube wall that serves as an ultrasonic entry zone for accessing the tube wall; and
   (e) means to receive defect-reflected sound returning from the entry zone on said tube wall to detect defects within the tube wall,
   wherein said first plurality of ultrasonic elements are arcuately deployed side-by-side to each other in a 1-dimensional arcuate array, in the shape of a portion of the circumferential surface of an imaginary cone, and wherein said elements provide ultrasonic beams that are directed to strike an outer surface of said tube at said entry zone from a plurality of approaching bearing angles, at an angle of incidence that will permit said beams to penetrate within the tube wall of said tube positioned beneath the acoustic coupling means.

9. The system in claim 8 wherein the beams emitted by the one or more probes all strike the entry zone at the same angle of incidence with respect to the outer surface of said tube.

10. The system in claim 8 wherein said one or more probes comprise two probes incorporated within a module, such module containing a mirror image ultrasonic phased array probe pair, the ultrasonic elements of each member of the pair being deployed along a common circular arc lying along a common conical surface.

11. The system in claim 8 comprising a single probe wherein the arcuate array is a circular arc which spans 360 degrees.

12. The system in claim 8 wherein at least one of said one or more modules contains at least one single-element ultrasonic element positioned to direct a sonic beam along the axis of said imaginary cone.

13. The system in claim 8 wherein said one or more probes comprise a second plurality of ultrasonic elements positioned with respect to said first plurality of ultrasonic elements to provide, collectively, a two-dimensional array of ultrasonic elements.

14. A system as in claim 13 wherein said second plurality of ultrasonic elements are deployed along the surface of said imaginary cone adjacent said first plurality of elements.

15. A system as in claim 8 comprising means to convey said tube longitudinally past said one or more modules while causing said tube to rotate about a longitudinal axis of said tube.

16. The system in claim 8 comprising means to rotate said tube being inspected about a longitudinal axis of said tube and means to move said one or more modules longitudinally with respect to said tube.

17. A method of non-destructive testing for defects in the wall of a tube as an inspected member to be inspected comprising:

(a) presenting the wall of such tube to a phased array (PA) ultrasonic probe system at an inspection station;

(b) causing the inspected member to be rotated continuously while said member is moving past said inspection station;

(c) including at the inspection station at least one ultrasonic phased array probe having ultrasonic elements that provide a plurality of focused ultrasonic beams which are directed at an entry zone on an outer surface of the tube wall that accesses an inspection volume within said tube wall, said beams arriving at the entry zone at a constant inspection angle along a plurality of conically oriented paths;

(d) causing said beams to enter the inspection volume within the wall of the tube whereby sonic reflections are created by defects within the inspection volume; and (e) detecting said reflections with an arcuately deployed array of ultrasonic sensors positioned to receive such reflections.

18. A method as in claim 17 wherein the ultrasonic elements within said at least one probe lie on a common conical support surface.

* * * * *